(12) United States Patent
Lee et al.

(10) Patent No.: US 11,771,912 B2
(45) Date of Patent: Oct. 3, 2023

(54) CANCER TREATMENT DEVICE

(71) Applicant: ELECTRONICS AND TELECOMMUNICATIONS RESEARCH INSTITUTE, Daejeon (KR)

(72) Inventors: Dae-Sik Lee, Daejeon (KR); Hyung Ju Park, Suwon-si (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 224 days.

(21) Appl. No.: 17/212,579

(22) Filed: Mar. 25, 2021

(65) Prior Publication Data
US 2021/0308476 A1 Oct. 7, 2021

(30) Foreign Application Priority Data
Apr. 1, 2020 (KR) .......................... 10-2020-0039623

(51) Int. Cl.
*A61N 1/40* (2006.01)
(52) U.S. Cl.
CPC ........................................ *A61N 1/40* (2013.01)
(58) Field of Classification Search
CPC . A61N 1/40; A61N 1/403; A61N 1/08; A61N 1/36002; A61N 1/406; A61B 5/01; A61K 41/0052; A61P 35/00
See application file for complete search history.

(56) References Cited

U.S. PATENT DOCUMENTS

| 8,382,749 | B2 | 2/2013 | Dunning et al. |
| 8,465,533 | B2 | 6/2013 | Palti |
| 8,706,261 | B2 | 4/2014 | Palti |
| 10,821,283 | B2 | 11/2020 | Giladi et al. |
| 2003/0032995 | A1 | 2/2003 | Handy et al. |

(Continued)

FOREIGN PATENT DOCUMENTS

| JP | 2003243736 A | 8/2003 |
| JP | 2008279259 A | 11/2008 |

(Continued)

OTHER PUBLICATIONS

Laihui Luo et al., "Growth and characteristics of Mn-doped PMN PT single crystals", Solid State Communications, 149(2009) pp. 978-981.

(Continued)

*Primary Examiner* — Mark W. Bockelman
(74) *Attorney, Agent, or Firm* — Rabin & Berdo, P.C.

(57) ABSTRACT

Provided is a cancer treatment device which includes a first electrode and a second electrode, which are electrically connected to a signal generator and face each other with a target area therebetween, and a temperature sensor which is electrically connected to the signal generator and disposed adjacent to the target area. A cancer cell is present in the target area. The signal generator applies an AC voltage between the first electrode and the second electrode to generate an electric field between the first electrode and the second electrode. The signal generator changes an intensity of the electric field on the basis of a temperature detected from the temperature sensor. Each of the first electrode and the second electrode includes a ferroelectric material doped with manganese.

16 Claims, 8 Drawing Sheets

(56) References Cited

U.S. PATENT DOCUMENTS

| | | | |
|---|---|---|---|
| 2003/0222943 A1 | 12/2003 | Sumi | |
| 2004/0176804 A1* | 9/2004 | Palti | A61N 1/326 607/2 |
| 2004/0210289 A1* | 10/2004 | Wang | A61K 9/5094 607/116 |
| 2005/0209642 A1* | 9/2005 | Palti | A61N 1/326 607/2 |
| 2013/0029354 A1 | 1/2013 | Cho et al. | |
| 2017/0281934 A1* | 10/2017 | Giladi | A61N 1/32 |
| 2018/0220986 A1 | 8/2018 | Choi et al. | |

FOREIGN PATENT DOCUMENTS

| | | |
|---|---|---|
| KR | 1020160134469 A | 11/2016 |
| KR | 1020170028601 A | 3/2017 |
| KR | 1020180133431 A | 12/2018 |
| KR | 20200034588 A | 3/2020 |

OTHER PUBLICATIONS

Roger Stupp et al., "Effect of Tumor-Treating Fields Plus Maintenance Temozolomide vs Maintenance Temozolomide Alone on Survival in Patients With Glioblastoma," JAMA, vol. 318, No. 23, Dec. 2017, pp. 2306-2316.

"The Development of Core Technologies for Wearable Cancer Treatment Device using Electric Field". Electronics And Telecommunications Research Institute.

Hyun-Taek Oh et al., Mn-Modified PMN-PZT [Pb(Mg1/3Nb2/3)O3-Pb(Zr, Ti)O3] Single Crystals for High Power Piezoelectric Transducers. Journal of the Korean Society vol. 54, No. 2. pp. 150-157, 2017.

* cited by examiner

Comparative Example 1

Comparative Example 2

Comparative Example 3

Experimental Example

CANCER TREATMENT DEVICE

CROSS-REFERENCE TO RELATED APPLICATIONS

This U.S. non-provisional patent application claims priority under 35 U.S.C. § 119 of Korean Patent Application No. 10-2020-0039623, filed on Apr. 1, 2020, the entire contents of which are hereby incorporated by reference.

BACKGROUND

The present disclosure herein relates to a cancer treatment device.

At present, physical surgical removal, chemical therapy, and radiation therapy are mainly used as general cancer treatment methods. However, the cancer treatment methods used currently may damage even normal tissues, and this causes an increase in intense pain to a patient, inconvenience of hospitalization or outpatient treatment, and high cost expenditure. Accordingly, the quality of life for cancer patients may be degraded. Thus, a research on treatment methods for improving efficacy of cancer treatment and enhancing the quality of life for cancer patients has been actively performed.

SUMMARY

The present disclosure provides a structure of a cancer treatment device that effectively inhibits cell division of a cancer cell.

The object of the present disclosure is not limited to the aforesaid, but other objects not described herein will be clearly understood by those skilled in the art from following description.

An embodiment of the inventive concept provides a cancer treatment device including: a signal generator; a first electrode and a second electrode which are electrically connected to the signal generator and face each other with a target area therebetween, wherein a cancer cell is present in the target area; and a temperature sensor electrically connected to the signal generator and disposed adjacent to the target area, wherein the signal generator applies an AC voltage between the first electrode and the second electrode to generate an electric field between the first electrode and the second electrode, and the signal generator changes an intensity of the electric field on the basis of a temperature detected from the temperature sensor, wherein each of the first electrode and the second electrode includes a ferroelectric material doped with manganese.

In an embodiment, the ferroelectric material may include single crystalline PMN-PT(Pb($M_x$Nb$_y$)$O_3$—PbTiO$_3$).

In an embodiment, a surface of the ferroelectric material may be coated with noble metal.

In an embodiment, each of the first electrode and the second electrode may have a disc shape or a plate shape.

The ferroelectric material may be doped with about 0.1 wt % to about 10 wt % of the manganese.

The signal generator may include a waveform generating unit, and the waveform generating unit may be a direct digital synthesizer (DDS) signal generating module in the form of a single chip.

A frequency range of a waveform of the electric field may be about 10 kHz to about 500 kHz.

In an embodiment of the inventive concept, a cancer treatment device includes: a signal generator; a first electrode and a second electrode which are electrically connected to the signal generator and face each other with a target area therebetween, wherein a cancer cell and a nanoparticle probe are present in the target area; and a temperature sensor electrically connected to the signal generator and disposed adjacent to the target area, wherein the signal generator is configured to generate a first electric field in the target area to change orientation of the nanoparticle probe, and the signal generator is configured to change an intensity of the electric field on the basis of a temperature detected from the temperature sensor, wherein each of the first electrode and the second electrode includes a ferroelectric material doped with manganese.

In an embodiment, the nanoparticle probe may include: a ferroelectric particle; a passivation layer applied on the ferroelectric particle; and a plurality of biomarkers attached on the passivation layer, wherein the biomarkers target the cancer cell.

In an embodiment, the ferroelectric particle may have a diameter greater than about 0 nm and less than or equal to about 50 nm, and the ferroelectric particle may include at least one of BaTiO$_3$ and SrTiO$_3$.

In an embodiment, the signal generator may include a control unit, and the control unit may be configured to convert the first electric field to a second electric field, wherein the second electric field has a frequency different from that of the first electric field.

In an embodiment, the second electric field may inhibit cell division of the cancer cell and may not cause a change in orientation of the nanoparticle probe.

In an embodiment, the ferroelectric material may include single crystalline PMN-PT(Pb($M_x$Nb$_y$)$O_3$—PbTiO$_3$).

In an embodiment, the cancer treatment device may further include a third electrode and a fourth electrode which face each other with the target area therebetween, wherein the signal generator applies a second AC voltage between the third electrode and the fourth electrode to generate a second electric field between the third electrode and the fourth electrode.

Each of the third and fourth electrodes may include a single crystalline ferroelectric material doped with manganese.

In an embodiment, the ferroelectric material may include PMN-PT(Pb($M_x$Nb$_y$)$O_3$—PbTiO$_3$).

In an embodiment, a waveform of the first electric field may have a frequency different from that of a waveform of the second electric field.

In an embodiment, the second electric field may inhibit cell division of the cancer cell and may not change orientation of the nanoparticle probe.

BRIEF DESCRIPTION OF THE FIGURES

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION

Embodiments of the present disclosure will be described with reference to the accompanying drawings so as to sufficiently understand constitutions and effects of the present disclosure. The present disclosure may, however, be embodied in different forms and diversely modified, and should not be construed as limited to the embodiments set forth herein. Rather, these embodiments are provided so that this disclosure will be thorough and complete, and will fully convey the scope of the present disclosure to a person skilled in the art to which the present disclosure pertains. In the attached drawings, sizes of elements are enlarged rather than real sizes thereof for convenience of description, and ratios of respective elements may be exaggerated or reduced.

Unless otherwise defined, all terms used in embodiments of the inventive concept have the same meaning as commonly understood by one of ordinary skill in the art to which the present disclosure belongs. Hereinafter, the present disclosure will be described in detail by explaining embodiments of the inventive concept with reference to the accompanying drawing.

Figure 1:
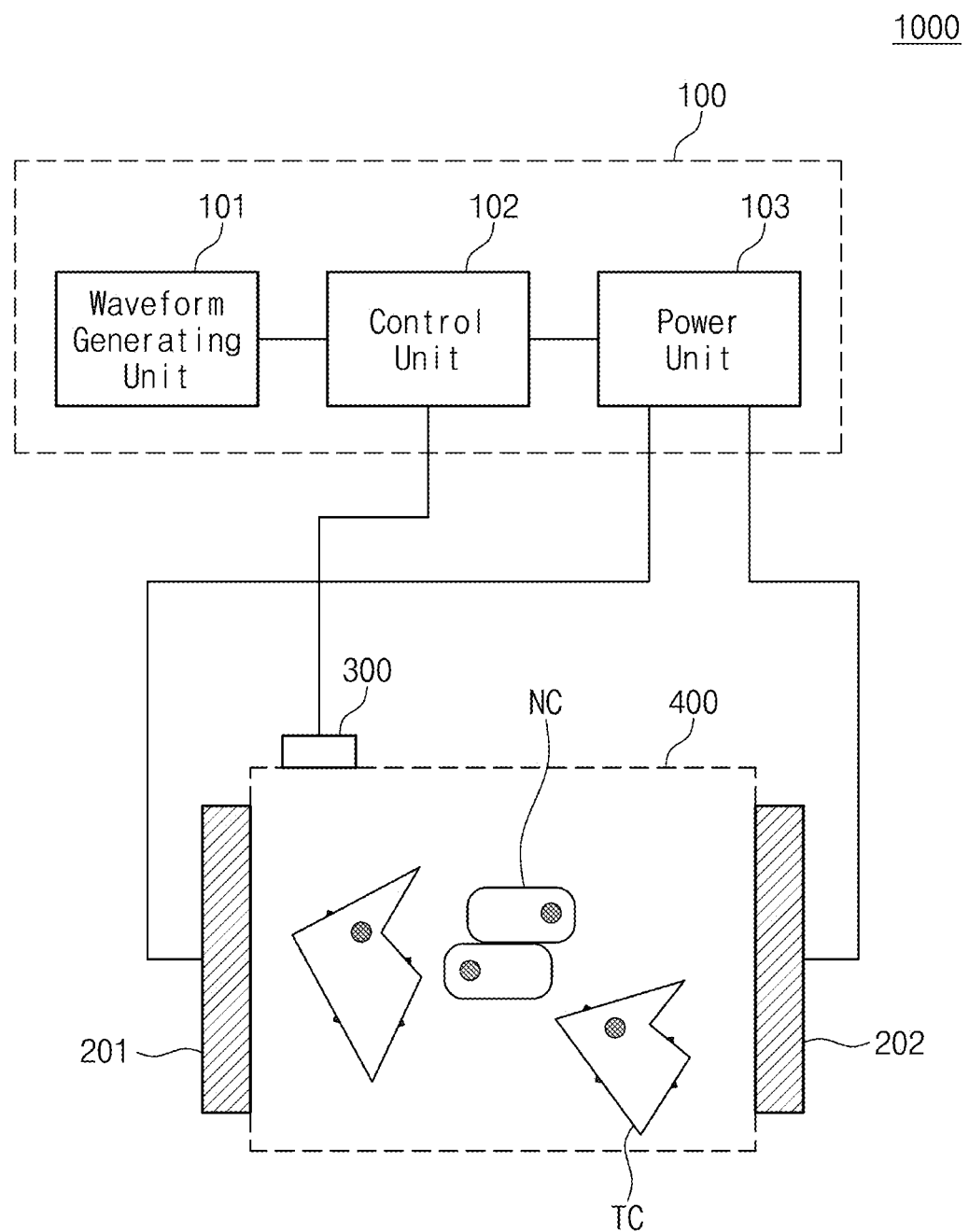
FIG. 1 is a conceptual diagram of a cancer treatment device according to an embodiment of the inventive concept.
Figure 2:
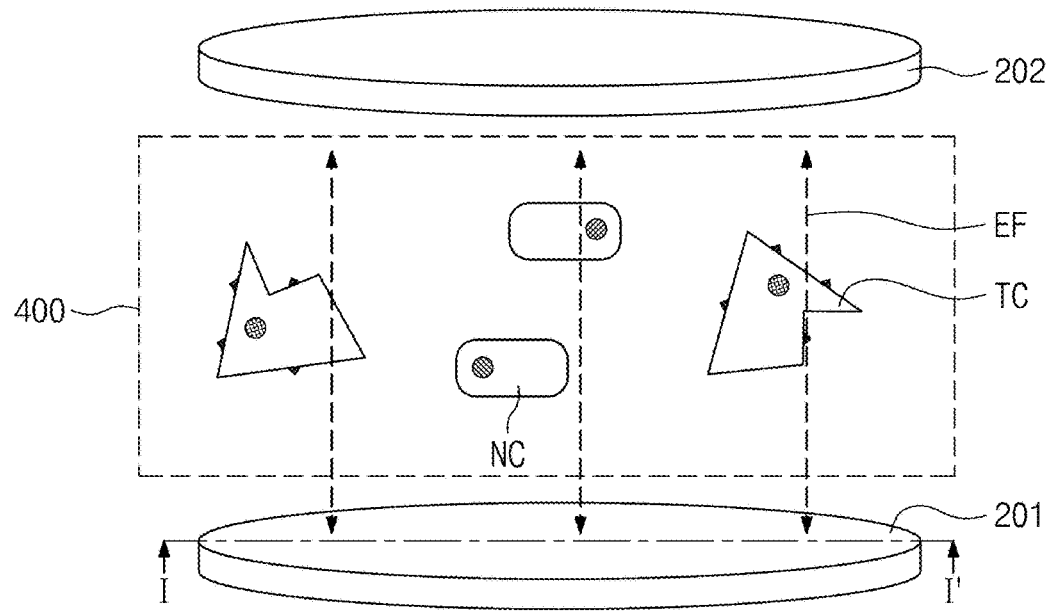
FIGS. 2 and 3 are conceptual diagrams showing pairs of electrodes and target areas according to embodiments.
Figure 3:
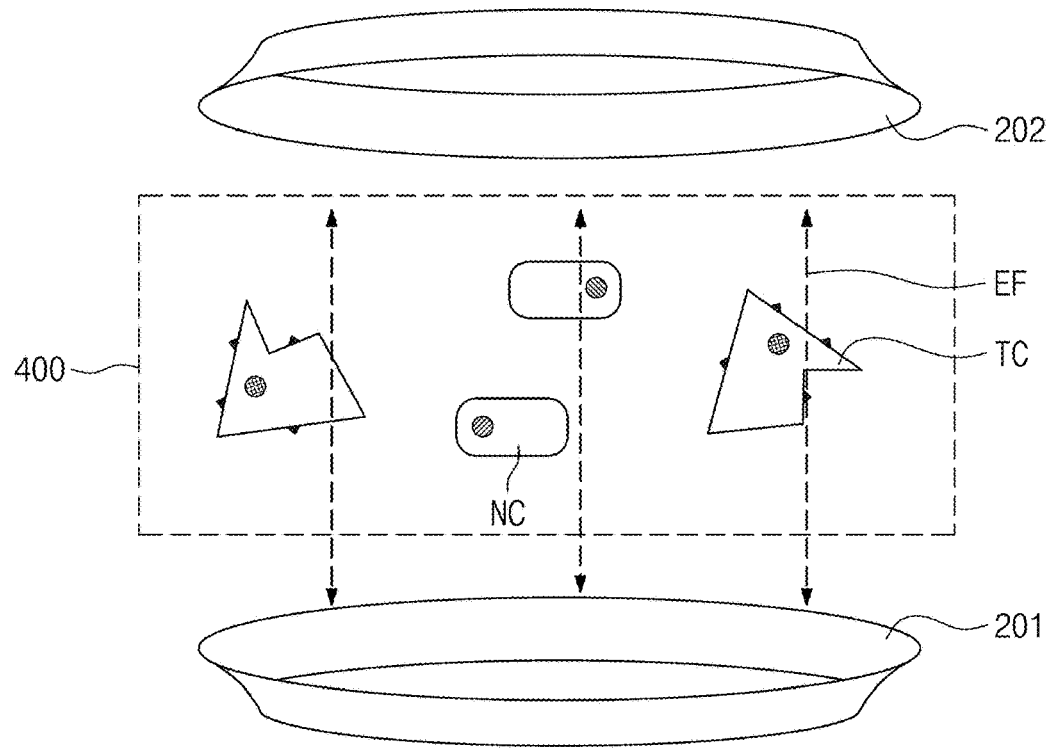
Figure 4:
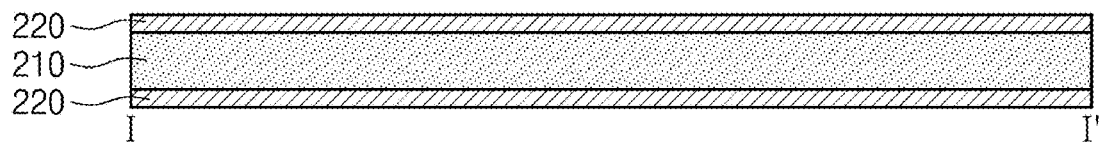
FIG. 4 is a cross-sectional view taken along line I-I' of FIG. 2.

FIG. 1 is a conceptual diagram of a cancer treatment device according to an embodiment of the inventive concept. FIGS. 2 and 3 are conceptual diagrams showing pairs of electrodes and target areas according to embodiments. FIG. 4 is a cross-sectional view taken along line I-I' of FIG. 2.

Referring to FIG. 1, a cancer treatment device 1000 according to an embodiment of the inventive concept may include a signal generator 100, a first electrode 201, a second electrode 202, and a temperature sensor 300.

The signal generator 100 may include a waveform generating unit 101, a control unit 102, and a power unit 103.

The waveform generating unit 101 may generate a waveform serving as the basis of a signal to be generated. The waveform generating unit 101 may be, for example, a direct digital synthesizer (DDS) waveform generating module in the form of a single chip. The waveform to be generated may be one of a sine wave, a triangular wave, or a square wave.

The control unit 102 may be electrically connected to the waveform generating unit 101, the temperature sensor 300, and the power unit 103. The control unit 102 may determine an amplitude, a frequency, etc. of the waveform transmitted from the waveform generating unit 101. The frequency range of the waveform may be determined as about 10 kHz to about 500 kHz. The amplitude of the waveform may be determined as greater than about 0 V/cm and less than or equal to about 100 V/cm. It is desirable that the amplitude of the waveform is determined as greater than about 0 V/cm and less than or equal to about 4 V/cm. The control unit 102 may be, for example, a proportional-integral-derivative (PID) control module.

Basically, the control unit 102 may transmit, to the power unit 103, information about the waveform transmitted from the waveform generating unit 101.

Also, the control unit 102 may change the transmitted waveform and transmit the changed waveform to the power unit 103. The control unit 102 includes a filter, and the waveform may be changed to a waveform having information about another waveform and/or frequency while passing through the filter. For example, as the control unit 102 includes an RC low pass filter, high frequency components may be reduced. The control unit 102 may receive feedback from the temperature sensor 300 to regulate the waveform so that a temperature of a diseased area (a target area) 400 does not exceed a set temperature.

The power unit 103 may be an AC power supply. The power unit 103 may be electrically connected to the first electrode 201 and the second electrode 202. The control unit 102 may apply an AC voltage between the first electrode 201 and the second electrode 202 through the power unit 103. Electric current may be regulated to be greater than about 0 mA and less than or equal to about 20 mA by the control unit 102.

In FIGS. 1, 2, and 3, the first electrode 201 and the second electrode 202 may be disposed spaced apart from each other with the diseased area 400 therebetween. The diseased area 400 may be an area in which cancer cells TC are present. In the diseased area 400, normal cells NC may also be present. The diseased area 400 may be, for example, an area of the brain, the breast, the lung, or the like in which the cancer cell TC is present.

At least a portion of the first electrode 201 and at least a portion of the second electrode 202 may face each other. As in FIG. 2, a first electrode 201 and a second electrode 202 may have a disc shape. Also, as in FIG. 3, a first electrode 201 and a second electrode 202 may have a plate shape.

In FIGS. 2 and 4, each of the first electrode 201 and the second electrode 202 may include a single crystalline ferroelectric layer 210 doped with manganese (Mn). The first electrode 201 and the second electrode 202 may include at least one of PMN-PT(Pb($M_x Nb_y$)$O_3$—PbTiO$_3$), PMN-PZT (Pb(Mg$_{1/3}$Nb$_{2/3}$)O$_3$—PbZrO$_3$—PbTiO$_3$), and BaTiO$_3$. A mass ratio of the manganese inside the single crystalline ferroelectric layer 210 doped with manganese may be about 0.1 wt % to about 10 wt %. For example, the first electrode 201 and the second electrode 202 may include single crystalline PMN-PT doped with about 5 wt % of manganese. A surface of the ferroelectric layer 210 doped with the manganese may be thinly coated with a noble metal layer 220. The noble metal layer 220 may include gold, silver, or etc. According to embodiments, the noble metal layer 220 may be omitted.

During cell division, microtubules having dipole moment are coupled to each other by an electrical force to form spindles, and as chromosomes arranged in the center of a cell are pulled toward both sides directions by the formed spindles, the cell division is completed. If the cell division is suppressed in the cancer cell, it is possible to treat a cancer through inhibition of cell division of the cancer cell.

In FIGS. 2 and 3, an electric field EF is formed between the first electrode 201 and the second electrode 202 by an AC voltage. A direction of the electric field EF may be continuously changed according to the amplitude and frequency of the AC voltage.

The cell division of the cancer cell TC may be inhibited by the electric field EF. The electric field EF may have a frequency that affects cell functions of the cancer cell. The frequency of the electric field EF may target a cell division cycle of the cancer cell.

For one example, orientation of microtubules inside spindles having dipole moment is deformed during the metaphase of division of the cancer cell TC, and thus at least some of the spindles may be broken. As the spindles are broken, the spindles may not be connected to chromosomes.

For another example, cleavage furrows may be formed during the telophase of the cancer cell division. Polar cell materials may be present inside a first preliminary daughter cell and a second preliminary daughter cell with two facing cleavage furrows therebetween. At least some of the polar cell materials may be moved between the two cleavage furrows by the electric field EF. In this case, the cancer cell may be prevented from contracting between the cleavage furrows and thus prevented from being divided into two daughter cells.

When the AC voltage is applied to electrodes including a ferroelectric material, the electric field is generated therebetween, and thus the cell division of cancer cell may be inhibited. When conductive electrodes are used, the temperature may be increased by application of high AC voltage, which may be high enough to cause burn injuries. Regarding the electrodes having the ferroelectric material, the treatment can be performed by the electric field without the rise in temperature. In particular, since the cancer treatment device 1000 according to an embodiment of the inventive concept includes an electrode having a single crystalline PMN-PT doped with manganese, the removal efficiency of cancer cells is enhanced, and the power consumption may be reduced by about 10% or more.

Referring to FIG. 1 again, the temperature sensor 300 may measure the temperature of the skin on the diseased area 400 and provide temperature information to the control unit 102. The temperature sensor 300 may regulate the intensity of the electric field EF through the control unit 102 and the power unit 103 so that the temperature of the diseased area 400 is maintained constant or the temperature of the diseased area 400 is not allowed to rise above a specific temperature to prevent burn injuries. The temperature sensor 300 may be a type of a negative temperature coefficient (NTC) thermistor.

The cancer treatment device 1000 according to the embodiment of the inventive concept includes the pair of electrodes that include the ferroelectric material having the single crystalline structure and doped with manganese, and the electric field is formed between the electrodes, thereby enabling the inhibition of the cell division of cancer cell. Accordingly, damage to normal cells may be further reduced, and treatment time may be remarkably reduced. Thus, ultimately, the quality of life for patients may be enhanced.

Figure 5:
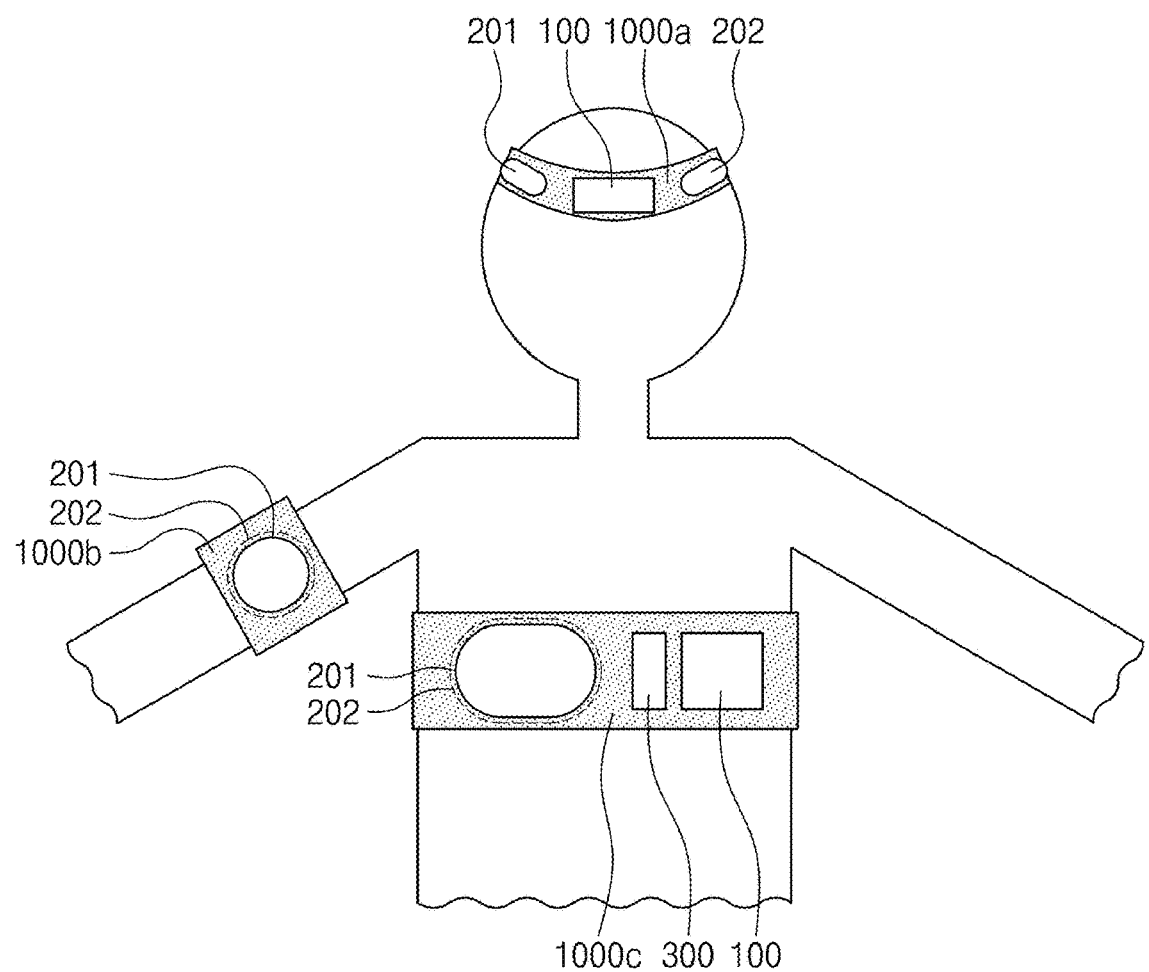
FIG. 5 is a view showing application examples of a cancer treatment device according to an embodiment of the inventive concept.

FIG. 5 is a view showing application examples of a cancer treatment device according to an embodiment of the inventive concept. Referring to FIG. 5, a cancer treatment device 1000 according to an embodiment of the inventive concept may include wearable-type cancer treatment devices 1000a, 1000b, and 1000c. The wearable-type cancer treatment devices 1000a, 1000b, and 1000c may be provided in the form which is freely attached to and detached from diseased areas of the human body (ex: the head, chest, arm, or the like) or diseased areas of an animal. As described above, the first electrode 201 and the second electrode 202 may be spaced apart from each other with the diseased area therebetween and apply the electric field into the diseased area.

Figure 6:
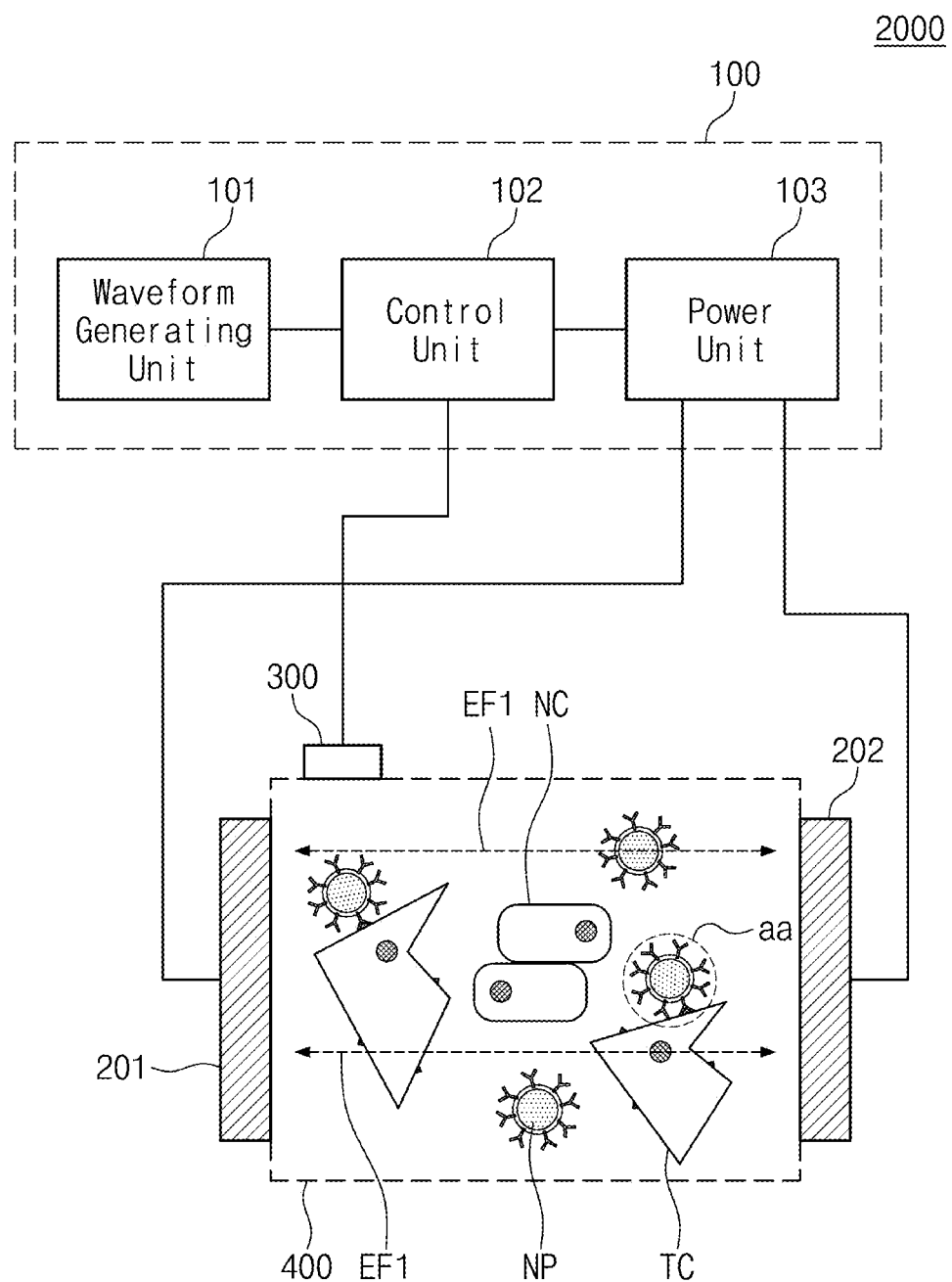
FIG. 6 is a conceptual diagram of a cancer treatment device according to embodiments.
Figure 7:
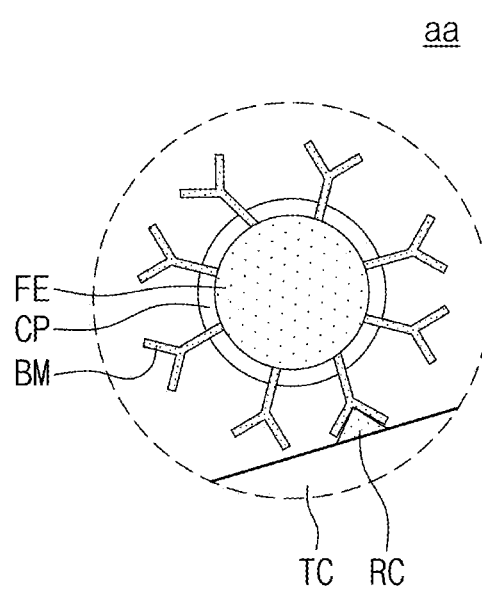
FIG. 7 is an enlarged view of a region "aa" of FIG. 6.

FIG. 6 is a conceptual diagram of a cancer treatment device according to embodiments. FIG. 7 is an enlarged view of a region "aa" of FIG. 6. Except for features described below, other features have been described with reference to FIGS. 1 to 4, and thus their duplicated descriptions will be omitted.

Referring to FIGS. 6 and 7, a plurality of nanoparticle probes NP may be injected around cancer cells TC and/or into the cancer cells TC. The nanoparticle probes NP may enter the human body through ingestive action or injection operation and move to a diseased area 400. Each of the nanoparticle probes NP may include a ferroelectric particle FE and a plurality of biomarkers BM. Each of the nanoparticle probes NP may further include a passivation layer CP as necessary.

The ferroelectric particle FE may have a spherical shape with a diameter greater than about 0 nm and less than or equal to about 200 nm. As long as the ferroelectric properties are maintained, the ferroelectric particle FE having a smaller diameter may be more effective. The ferroelectric particle FE may include at least one of $BaTiO_3$ and $SrTiO_3$.

The biomarkers BM may be attached to the ferroelectric particle FE. The nanoparticle probe NP may be coupled to a receptor RC on the surface of the cancer cell TC through the biomarkers BM.

The nanoparticle probe NP coupled to the receptor RC of the cancer cell TC may be maintained in this state or may enter the cancer cell TC through phagocytosis of the cancer cell TC.

The passivation layer CP may cover the surface of the ferroelectric particle FE. The passivation layer CP may prevent a non-specific binding reaction of the nanoparticle probe NP. The passivation layer CP may include, for example, fetal bovine serum (FBS).

A first electric field EF1 may be applied to the nanoparticle probe NP. The first electric field EF1 may have a frequency different from that of the electric field EF described above in FIGS. 1 to 3. In addition, according to embodiments, the first electric field EF1 may have an amplitude different from that of the electric field EF. The frequency of the first electric field EF1 may be lower than the frequency of the electric field EF. The first electric field EF1 may selectively change the orientation of the nanoparticle probe NP. Unlike the electric field EF, the first electric field EF1 may not affect the cell functions of the cancer cell TC itself.

When the first electric field EF1 is applied to the nanoparticle probe NP, the ferroelectric particle FE may be subjected to an electric force. As a result, the orientation of the nanoparticle probe NP may be changed. In this specification, the change (F) in orientation may include all of vibration, rotation, and translation of the nanoparticle probe NP. As the orientation of the nanoparticle probe NP is changed, the cell division of the cancer cell TC may be inhibited.

For example, during the metaphase of division of the cancer cell TC, the polarized nanoparticle probe NP may be moved adjacent to microtubules inside spindles by electrical attraction thereto. The nanoparticle probe NP may be positioned into the cytoplasm of cancer cell. The nanoparticle probe NP may affect the cancer cell TC by using the electrical characteristics exhibited by the first electric field EF1. For one example, at least some of the chromosomes may not be coupled to the centrosomes due to the electric field around the nanoparticle probe NP. Also, the spindles extending from the centrosomes may not be connected to the chromosomes due to steric hindrance of the nanoparticle probes NP. The spindles may not be connected to the chromosomes due to the vibration, rotation, or the like of the nanoparticle probes NP.

For another example, cleavage furrows may be formed during the telophase of the cancer cell division. The nanoparticle probes NP may be moved by the first electric field EF1, and at least some of the nanoparticle probes NP may be moved between two cleavage furrows. The cancer cell may be prevented from contracting between the cleavage furrows and thus prevented from being divided into two daughter cells.

A control unit 102 may change the first electric field EF1 to a second electric field (not shown). The second electric field may be the same as the electric field EF illustrated through FIGS. 1 to 3. That is, the second electric field may affect functions of the cancer cells TC by targeting cell division cycles of the cancer cells TC, but may not change the orientation of the nanoparticle probes NP. The division of cancer cell may be inhibited by applying the second electric field as well as the first electric field EF1 to the diseased area 400.

According to another embodiment, the first electric field EF1 and the second electric field may have the same frequency. In this case, the nanoparticle probe NP may be configured such that the orientation thereof is changed even by the second electric field.

A cancer treatment device 2000 according to an embodiment of the inventive concept uses the nanoparticle probe NP and uses two or more electric fields (the first electric field and the second electric field), and thus the cancer treatment effect may be further improved. In particular, as the cancer treatment device 2000 includes electrodes 201 and 202 including a single crystalline PMN-PT doped with manganese, the cancer treatment effect may be maximized.

Figure 8:
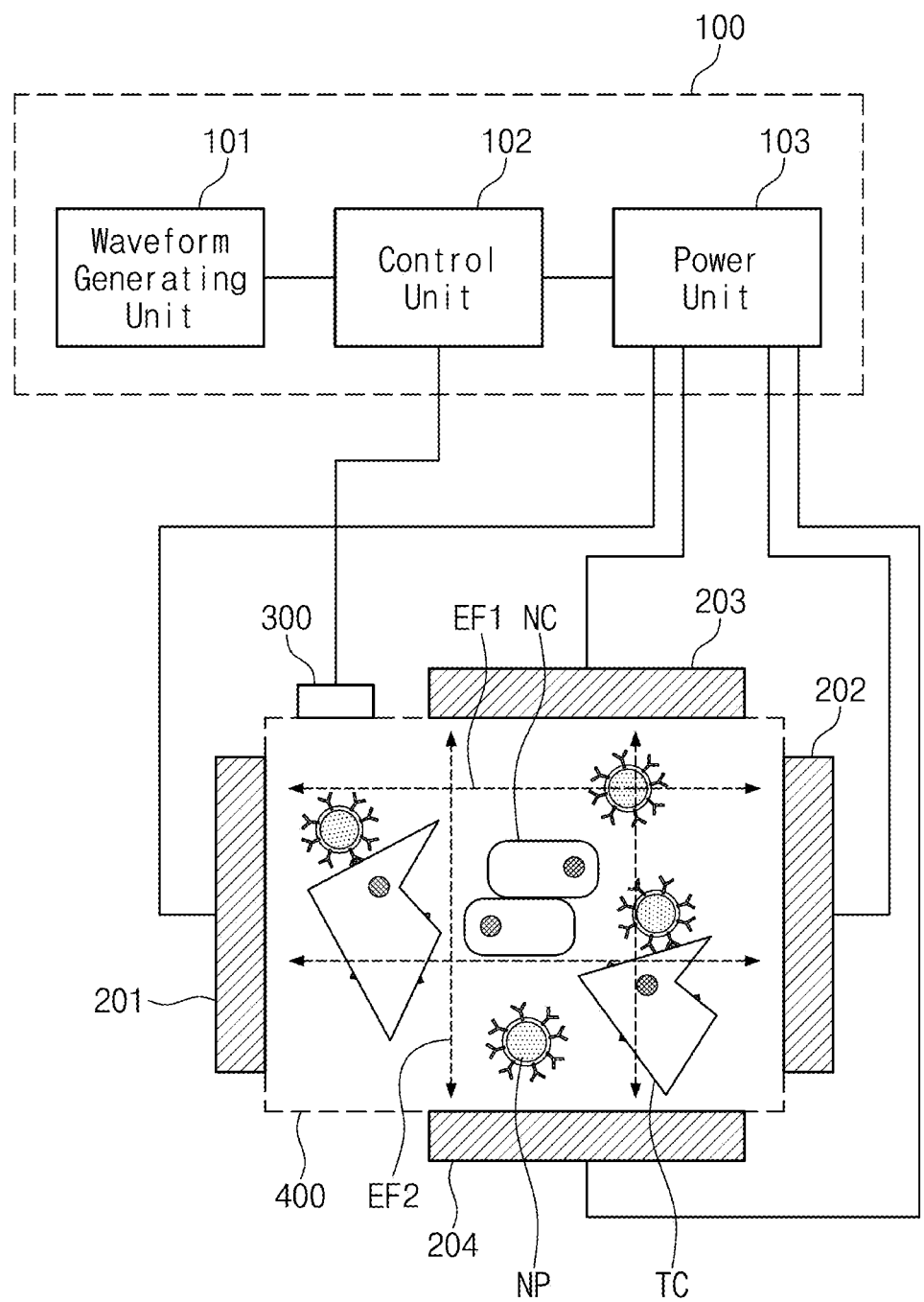
FIG. 8 is a conceptual diagram of a cancer treatment device according to embodiments.

FIG. 8 is a conceptual diagram showing a cancer treatment device according to embodiments. Except for features described below, other features have been described in detail with reference to FIGS. 1 to 6, and thus their duplicated descriptions will be omitted.

Referring to FIG. 8, a cancer treatment device 3000 according to an embodiment of the inventive concept may include a signal generator 100, a first electrode 201, a second electrode 202, a third electrode 203, a fourth electrode 204, and a temperature sensor 300. The first electrode 201 and the second electrode 202 may face each other with a diseased area 400 therebetween. The third electrode 203 and the fourth electrode 204 may face each other with a diseased area 400 therebetween. According to another embodiment, one of the third electrode 203 or the fourth electrode 204 may be omitted.

The first to fourth electrodes 201, 202, 203, and 204 may have a disc shape or a plate shape as in FIGS. 2 and 3. The first to fourth electrodes 201, 202, 203, and 204 may have a single crystalline ferroelectric layer 210 doped with manganese (Mn) as in FIG. 4. The first to fourth electrodes 201, 202, 203, and 204 may include at least one of PMN-PT(Pb(M$_x$Nb$_y$)O$_3$—PbTiO$_3$), PMN-PZT(Pb(Mg$_{1/3}$Nb$_{2/3}$)O$_3$—PbZrO$_3$—PbTiO$_3$), and BaTiO$_3$. For example, the first to fourth electrodes 201, 202, 203, and 204 may include single crystalline PMN-PT doped with about 5 wt % of manganese. As in FIG. 4, a surface of the ferroelectric layer 210 doped with manganese may be thinly coated with a noble metal layer 220. The noble metal layer 220 may include gold, silver, or etc. According to embodiments, the noble metal layer 220 may be omitted.

A first electric field EF1 may be generated between the first electrode 201 and the second electrode 202. A second electric field EF2 may be generated between the third electrode 203 and the fourth electrode 204. The first electric field EF1 and the second electric field EF2 may be individually generated. The first electric field EF1 and the second electric field EF2 may be simultaneously applied to the diseased area 400 or alternately applied to the diseased area 400.

For example, when the first electric field EF1 and the second electric field EF2 are alternately applied to the diseased area 400, a more uniform electric field may be applied, and the inhibition effect on cell division of the cancer cell through a nanoparticle probe NP may increase.

The first electric field EF1 and the second electric field EF2 may have frequencies different from each other. The first electric field EF1 may have a specific frequency that causes a change in orientation of the nanoparticle probe NP. The first electric field EF1 may have a frequency in a range from about 10 kHz to about 500 kHz.

As described above, the nanoparticle probe NP in the first electric field EF1 may prevent the connection of centrosomes and chromosomes through spindles during cell division and prevent the generation of daughter cells, and thus the cell division of a cancer cell TC may be inhibited.

The second electric field EF2 may have a specific frequency that causes a change in orientation of polar materials of the cancer cell TC. The second electric field EF2 may have a frequency in a range from about 10 kHz to about 500 kHz.

During the metaphase of division of the cancer cell TC, the spindles may be broken by the orientation of microtubules due to the second electric field EF2. The polar cell materials are moved between the cleavage furrows by the second electric field EF2, and thus it is possible to prevent separation into two daughter cells.

According to another embodiment, the first electric field EF1 and the second electric field EF2 may have the same frequency. In this case, the nanoparticle probe NP may be configured such that the orientation thereof is changed even by the second electric field EF2.

The cancer treatment device 3000 according to an embodiment of the inventive concept applies the first electric field EF1 and the second electric field EF2 simultaneously, thereby enabling the effective inhibition of the division of cancer cell. In particular, as the cancer treatment device 3000 includes the electrodes 201 and 202 including a single crystalline PMN-PT doped with manganese, the cancer treatment effect may be maximized.

Figure 9:
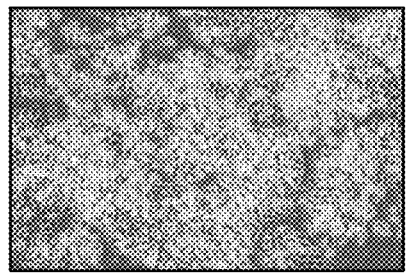
FIG. 9 illustrates images showing the relative number of lung cancer cells according to comparative examples and an experimental example.
Figure 9:
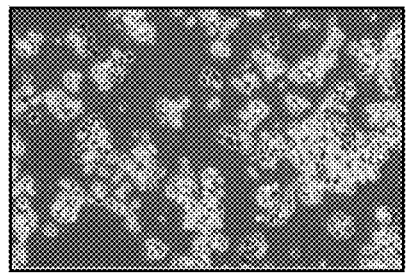
Figure 9:
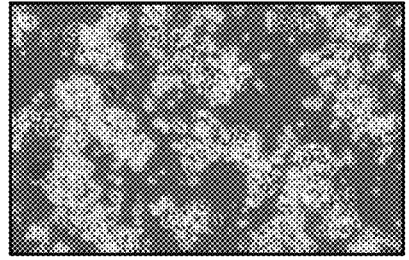
Figure 9:
Figure 10:
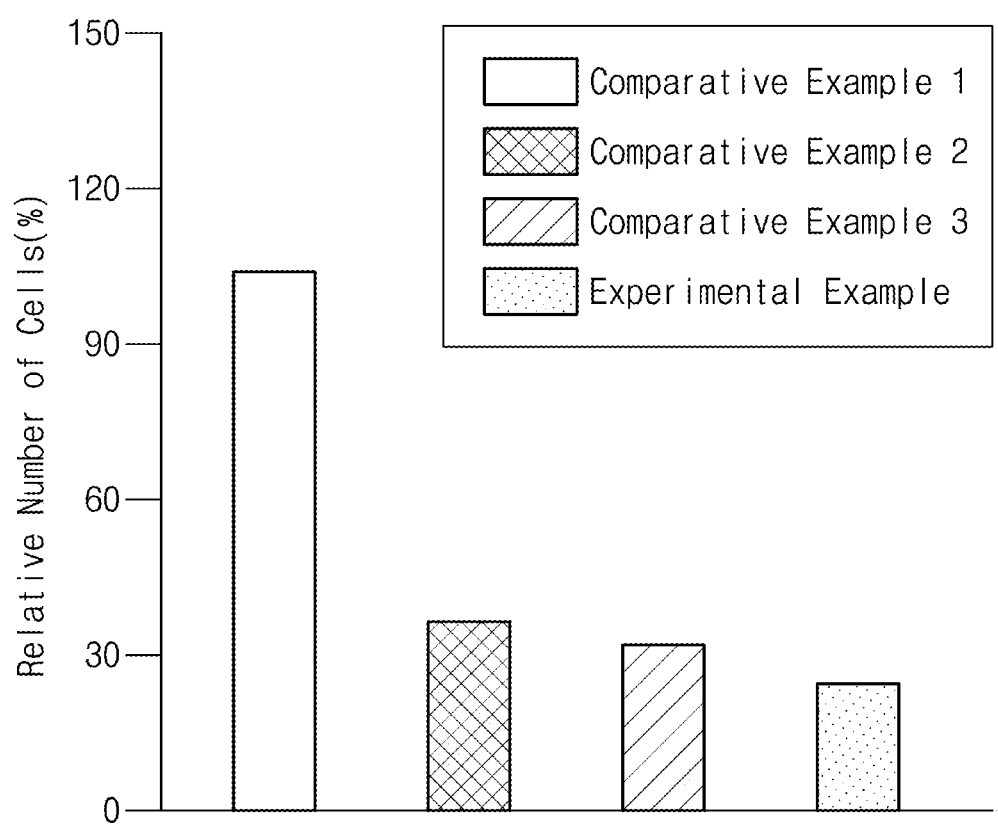
FIG. 10 is a graph showing the relative number of remaining lung cancer cells according to the comparative examples and the experimental example.

FIG. 9 illustrates images showing the relative number of lung cancer cells according to comparative examples and an experimental example. FIG. 10 is a graph showing the relative number of remaining lung cancer cells according to the comparative examples and the experimental example.

Comparative Example 1

A BT-549 breast cancer cell line was purchased from American Type Culture Collection (ATCC, Manassas, Va.) and prepared. BT-549 cells were cultured in RPMI (coming). The BT-549 cells are supplemented with 10% FBS and 1% penicillin/streptomycin. The BT-549 cells were maintained at about 37° C. in a humidified 5% $CO_2$ incubator.

The BT-549 cells were maintained for about 24 hours in a 22-mm plastic cover slip (Thermo Fisher Scientific, MA, USA). Then, the cover slip was transferred to a ceramic inovitro dish (NovoCure, Haifa, Israel) by using an autoclaved forceps.

Comparative Example 2

A dish was prepared in which cancer cells were cultured under the same condition as Comparative Example 1. Electric current having a frequency of about 150 kHz was applied for about 72 hours at a temperature of about 19° C. by using a commercialized tumor treatment filed (TFT) device.

Comparative Example 3

A dish was prepared in which cancer cells were cultured under the same condition as Comparative Example 1. An electrode subjected to an electric field was replaced with single crystalline PMN-PT, and electric current having a frequency of about 150 kHz was applied for about 72 hours at a temperature of about 19° C.

Experimental Example

A dish was prepared in which cancer cells were cultured under the same condition as Comparative Example 1. An electrode subjected to an electric field was replaced with single crystalline PMN-PT doped with about 5 wt % of manganese, and electric current having a frequency of about 150 kHz was applied for about 72 hours at a temperature of about 19° C.

Referring to FIGS. 9 and 10, a greater number of cancer cells were reduced in all of Comparative Example 2, Comparative Example, 3, and Experimental Example, in which electric fields are applied, compared to Comparative Example 1 in which an electric field is not applied. In particular, it was confirmed that the fewest number of cancer cells remain in Experimental Example in which the electrode of the single crystalline PMN-PT doped with manganese is used.

The cancer treatment device according to the embodiment of the inventive concept includes the pair of electrodes that include the ferroelectric material having the single crystalline structure and doped with manganese, and the electric field therebetween may effectively inhibit cell division of the cancer cell.

Although the embodiments of the inventive concept are described with reference to the accompanying drawings, those with ordinary skill in the technical field to which the inventive concept pertains will understand that the present disclosure can be carried out in other specific forms without changing the technical idea or essential features. Thus, the above-described embodiments are to be considered illustrative and not restrictive to all aspects.

What is claimed is:

1. A cancer treatment device comprising:
   a signal generator;
   a first electrode and a second electrode which are electrically connected to the signal generator and face each other with a target area therebetween, wherein the target area is adapted to receive a cancer cell therein; and
   a temperature sensor electrically connected to the signal generator and disposed adjacent to the target area,
   wherein the signal generator applies an AC voltage between the first electrode and the second electrode to generate an electric field between the first electrode and the second electrode, and
   the signal generator changes an intensity of the electric field on the basis of a temperature detected from the temperature sensor,
   wherein each of the first electrode and the second electrode comprises a ferroelectric material doped with manganese.

2. The cancer treatment device of claim 1, wherein the ferroelectric material comprises single crystalline PMN-PT $(Pb(M_xNb_y)O_3—PbTiO_3)$.

3. The cancer treatment device of claim 1, wherein a surface of the ferroelectric material is coated with noble metal.

4. The cancer treatment device of claim 1, wherein each of the first electrode and the second electrode has a disc shape or a plate shape.

5. The cancer treatment device of claim 1, wherein a doping amount of the manganese is about 0.1 wt % to about 10 wt %.

6. The cancer treatment device of claim 1, wherein the signal generator comprises a waveform generating unit, and the waveform generating unit is a direct digital synthesizer (DDS) signal generating module in the form of a single chip.

7. The cancer treatment device of claim 1, wherein a frequency range of a waveform of the electric field is about 10 kHz to about 500 kHz.

8. A cancer treatment device comprising:
   a signal generator;
   a first electrode and a second electrode which are electrically connected to the signal generator and face each other with a target area therebetween, wherein the target area is adapted to receive a cancer cell and a nanoparticle probe therein; and
   a temperature sensor electrically connected to the signal generator and disposed adjacent to the target area,
   wherein the signal generator is configured to generate a first electric field in the target area to change orientation of the nanoparticle probe, and
   the signal generator is configured to change an intensity of the electric field on the basis of a temperature detected from the temperature sensor,
   wherein each of the first electrode and the second electrode comprises a ferroelectric material doped with manganese.

9. The cancer treatment device of claim 8, wherein the nanoparticle probe comprises:
   a ferroelectric particle;
   a passivation layer applied on the ferroelectric particle; and
   a plurality of biomarkers attached on the passivation layer,
   wherein the biomarkers target the cancer cell.

10. The cancer treatment device of claim 9, wherein the ferroelectric particle has a diameter greater than about 0 nm and less than or equal to about 50 nm, and
    the ferroelectric particle comprises at least one of $BaTiO_3$ and $SrTiO_3$.

11. The cancer treatment device of claim 8, wherein the signal generator comprises a control unit, and
    the control unit is configured to convert the first electric field to a second electric field,
    wherein the second electric field has a frequency different from that of the first electric field.

12. The cancer treatment device of claim 11, wherein the second electric field inhibits cell division of the cancer cell and does not cause a change in orientation of the nanoparticle probe.

13. The cancer treatment device of claim 8, further comprising a third electrode and a fourth electrode which face each other with the target area therebetween, wherein the signal generator applies a second AC voltage between the third electrode and the fourth electrode to generate a second electric field between the third electrode and the fourth electrode, and each of the third electrode and the fourth electrode comprises a single crystalline ferroelectric material doped with manganese.

14. The cancer treatment device of claim 13, wherein the ferroelectric material comprises PMN-PT(Pb($M_x Nb_y$)$O_3$—PbTiO$_3$).

15. The cancer treatment device of claim 13, wherein a waveform of the first electric field has a frequency different from that of a waveform of the second electric field.

16. The cancer treatment device of claim 13, wherein the second electric field inhibits cell division of the cancer cell and does not change orientation of the nanoparticle probe.

* * * * *